(12) United States Patent
Koyanagi et al.

(10) Patent No.: US 11,429,667 B2
(45) Date of Patent: Aug. 30, 2022

(54) DATA GENERATION METHOD, DATA STRUCTURE, AND COMPUTER-READABLE RECORDING MEDIUM

(71) Applicant: FUJITSU LIMITED, Kawasaki (JP)

(72) Inventors: Yusuke Koyanagi, Kawasaki (JP); Shinichiro Tago, Shinagawa (JP); Masaru Fuji, Musashino (JP)

(73) Assignee: FUJITSU LIMITED, Kawasaki (JP)

( * ) Notice: Subject to any disclaimer, the term of this patent is extended or adjusted under 35 U.S.C. 154(b) by 357 days.

(21) Appl. No.: 16/294,521

(22) Filed: Mar. 6, 2019

(65) Prior Publication Data
US 2019/0278806 A1    Sep. 12, 2019

(30) Foreign Application Priority Data

Mar. 7, 2018   (JP) .............................. JP2018-041324

(51) Int. Cl.
| | | |
|---|---|---|
| *G06F 16/00* | (2019.01) | |
| *G06F 16/901* | (2019.01) | |
| *G06N 3/08* | (2006.01) | |
| *G06N 20/00* | (2019.01) | |

(52) U.S. Cl.
CPC .......... *G06F 16/9024* (2019.01); *G06N 3/08* (2013.01); *G06N 20/00* (2019.01)

(58) Field of Classification Search
CPC ....... G06F 16/9024; G06N 20/00; G06N 3/08
See application file for complete search history.

(56) References Cited

U.S. PATENT DOCUMENTS

| | | | |
|---|---|---|---|
| 10,217,241 B2* | 2/2019 | Rossi ........................ | G06T 9/20 |
| 2005/0154533 A1 | 7/2005 | Smythe et al. | |
| 2009/0193044 A1* | 7/2009 | Buehrer .................. | G06F 16/95 |
| 2009/0318311 A1 | 12/2009 | Smythe et al. | |
| 2010/0257425 A1* | 10/2010 | Yue ..................... | H03M 13/033 |
| | | | 714/752 |
| 2012/0102034 A1* | 4/2012 | Kim ....................... | G06F 16/29 |
| | | | 707/E17.089 |

(Continued)

FOREIGN PATENT DOCUMENTS

| | | |
|---|---|---|
| JP | 1-267774 A | 10/1989 |
| JP | 2005-529382 | 9/2005 |
| JP | 2007-249297 | 9/2007 |

OTHER PUBLICATIONS

Takei et al., "Performance evaluation of large-scale web graph analysis by graph reconstruction", Information Processing Society of Japan, Nov. 19, 2015, pp. 1-6.

(Continued)

*Primary Examiner* — Usmaan Saeed
*Assistant Examiner* — David M Nafziger
(74) *Attorney, Agent, or Firm* — Staas & Halsey LLP

(57) ABSTRACT

A data generation method includes: with regard to a target in which a plurality of sets of reference source data and reference target data are connectable by using edges, extracting information that corresponds to a complete bipartite graph from the connected target; and when there are a plurality of sets of reference source data and a plurality of sets of reference target data that are the extracted information and that constitute the complete bipartite graph, generating a virtual node between the reference source data and the reference target data.

11 Claims, 17 Drawing Sheets

(56) References Cited

U.S. PATENT DOCUMENTS

2015/0019161 A1* 1/2015 Moriguchi .............. G07C 9/00
  702/150
2018/0176239 A1* 6/2018 Yan .................... H04L 63/1425
2020/0384061 A1* 12/2020 Sonoda .................. A61P 25/28

OTHER PUBLICATIONS

Araki et al., "Structural characterization and modeling of ncRNA-protein interactions", Information Processing Society of Japan, Feb. 15, 2010, pp. 1-8.

Japanese Office Action dated Oct. 5, 2021 from Japanese Patent Application No. 2018-041324.

* cited by examiner

FIG.1
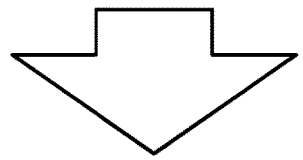
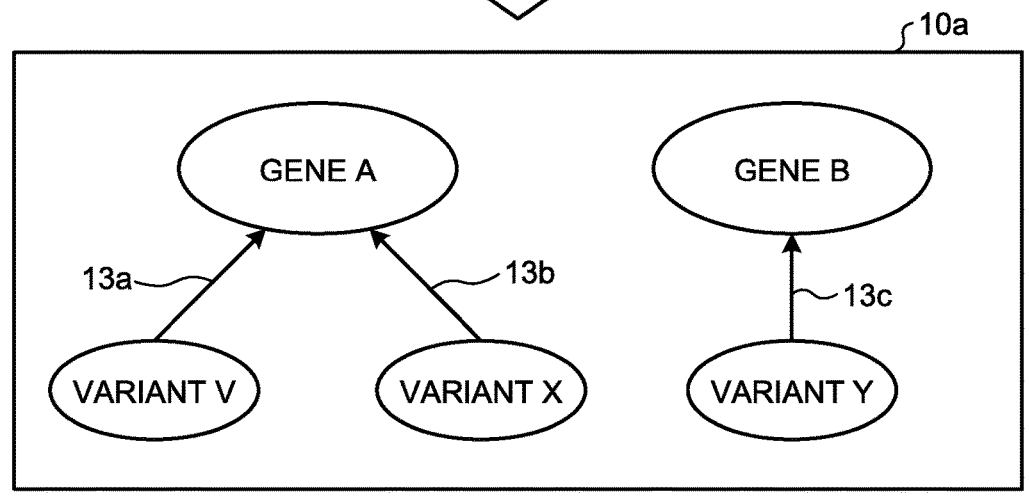

FIG.7

|221

| REFERENCE TARGET ID | PROTEIN ID | START POSITION | END POSITION | DOMAIN ID | ... |
|---|---|---|---|---|---|
| A | P0XXX1 | 4 | 132 | PF0XXX9 | |
| B | P0XXX1 | 5 | 134 | PF0XXY9 | |
| C | P0XXX1 | 6 | 182 | PF0XYY3 | |
| ... | | | | | |

FIG.8

|222

| REFERENCE SOURCE ID | COORDINATE | ... |
|---|---|---|
| 1 | 4 | |
| 2 | 4 | |
| 3 | 5 | |
| ... | | |

FIG.9

| REFERENCE TARGET ID | REFERENCE SOURCE ID |
|---|---|
| A | 1 |
| A | 2 |
| A | 3 |
| A | 4 |
| A | 5 |
| A | 6 |
| B | 4 |
| B | 5 |
| B | 6 |
| B | 7 |
| B | 8 |
| C | 8 |
| C | 9 |
| C | 10 |

FIG.10

| VIRTUAL NODE ID | REFERENCE TARGET ID |
|---|---|
| V1 | A |
| V1 | B |

FIG.11

| VIRTUAL NODE ID | REFERENCE TARGET ID | REFERENCE SOURCE ID |
|---|---|---|
| V1 | A, B | 4, 5, 6 |
| - | B, C | 8 |

| REFERENCE TARGET ID | REFERENCE SOURCE ID |
|---|---|
| A | 1 |
| A | 2 |
| A | 3 |
| V1 | 4 |
| V1 | 5 |
| V1 | 6 |
| B | 7 |
| B | 8 |
| C | 8 |
| C | 9 |
| C | 10 |

223y (rows V1/4, V1/5, V1/6)

223z (rows B/8, C/8)

FIG.17

| OVERLAPPED-REGION ID | PROTEIN ID | COMBINATION OF REGIONS | START POSITION | END POSITION |
|---|---|---|---|---|
| v11 | P0XXX1 | A, B | 5 | 132 |
| v12 | P0XXX1 | A, C | 6 | 132 |
| v13 | P0XXX1 | A, D | 9 | 132 |
| ... | | | | |
| v19 | P0XXX1 | A, B, C, D | 9 | 132 |
| ... | | | | |
| v91 | P0XXX9 | | | |
| ... | | | | |

FIG.18

| OVERLAPPED-REGION ID | PROTEIN ID | OVERLAPPED REGION | START POSITION | END POSITION | AMOUNT OF DATA | REDUCTION EFFECT |
|---|---|---|---|---|---|---|
| v11 | P0XXX1 | A, B | 5 | 132 | 861 | 859 |
| v12 | P0XXX1 | A, C | 6 | 132 | 854 | 852 |
| v13 | P0XXX1 | B, C | 9 | 132 | 836 | 834 |
| v14 | P0XXX1 | A, B, C | 6 | 132 | 854 | 1705 |
| ⋮ | | | | | | |
| v19 | P0XXX1 | A, B, C, D | 9 | 132 | 836 | 2504 |
| ⋮ | | | | | | |

| s | p | o |
|---|---|---|
| A | START COORDINATE | 4 |
| A | END COORDINATE | 132 |
| A | PROTEIN ID | P0XXX1 |
| A | DOMAIN ID | PF0XXX9 |
| ... | | |
| 1 | COORDINATE | 4 |
| ... | | |
| A | VARIANT | 1 |
| ... | | |

DATA GENERATION METHOD, DATA STRUCTURE, AND COMPUTER-READABLE RECORDING MEDIUM

CROSS-REFERENCE TO RELATED APPLICATION

This application is based upon and claims the benefit of priority of the prior Japanese Patent Application No. 2018-041324, filed on Mar. 7, 2018, the entire contents of which are incorporated herein by reference.

FIELD

The embodiment(s) discussed herein is (are) related to a data generation method, a data generation program, and a data structure.

BACKGROUND

In a database, a specific region in a sequence is sometimes related to data included in the region. There are, for example, any region in a sequence and data included in the region, e.g., a domain and an amino-acid variant in a protein, or a gene region and a base variant in a genome sequence. Data having such a correspondence relationship is used in, for example, machine learning processing, and it is used to determine the relation with the posed problem. Thus, there is a known technology for representing the correspondence relationship between a region and data.

For example, there is a known data management system that is capable of managing sharing or unsharing of data in units of files even between multiple storage means in separate locations. The system is configured by connecting multiple data management units in a network. A file shared in the data management system is associated with flag information for uniquely identifying each file in the system. Based on the flag information, the data management unit acquires a file associated with the flag information from a different data management unit.

Furthermore, there is a known method for molecular database search and directional molecular library design by using representation of a common three-dimensional structure of a protein surface while determining the feature of the common structure. With regard to analysis and representation of β turn, loop, and protein surface such as contact surface, the method identifies the common position and the orientation of an amino-acid side chain simplified as $C\alpha$-$C\beta$ vector. Furthermore, the method provides the feature of a common three-dimensional structure that is usable for searching a molecular database in order to identify the common region of a surface charge represented by grid points in the three-dimensional space and identify a molecule that matches the feature of the common three-dimensional structure of the protein.

Patent Document 1: Japanese Laid-open Patent Publication No. 2007-249297
Patent Document 2: Japanese National Publication of International Patent Application No. 2005-529382

The above-described technology has a problem of an enormous amount of data representing a correspondence relationship. For example, when the correspondence relationship between a region and data is represented by using a graph, or the like, including an edge and a node, the number of edges representing the correspondence relationship is sometimes increased.

SUMMARY

According to an aspect of an embodiment, a data generation method includes: with regard to a target in which a plurality of sets of reference source data and reference target data are connectable by using edges, extracting information that corresponds to a complete bipartite graph from the connected target; and when there are a plurality of sets of reference source data and a plurality of sets of reference target data that are the extracted information and that constitute the complete bipartite graph, generating a virtual node between the reference source data and the reference target data.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 is a diagram that illustrates an example of the relationship between a gene region in a genome sequence and a variant of a base;

FIG. 7 is a diagram that illustrates an example of a reference target DB according to the first embodiment;

FIG. 8 is a diagram that illustrates an example of a reference source DB according to the first embodiment;

FIG. 9 is a diagram that illustrates an example of a relationship DB according to the first embodiment;

FIG. 10 is a diagram that illustrates an example of a virtual node DB according to the first embodiment;

FIG. 11 is a diagram that illustrates an example of data used during a virtual-node determination process according to the first embodiment;

FIG. 12 is a diagram that illustrates an example of the relationship DB after a virtual node is generated according to the first embodiment;

FIG. 17 is a diagram that illustrates an example of the overlapped-region DB according to the second embodiment;

FIG. 18 is a diagram that illustrates an example of data used during a virtual-node selection process according to the second embodiment;

DESCRIPTION OF EMBODIMENTS

Figure 2:
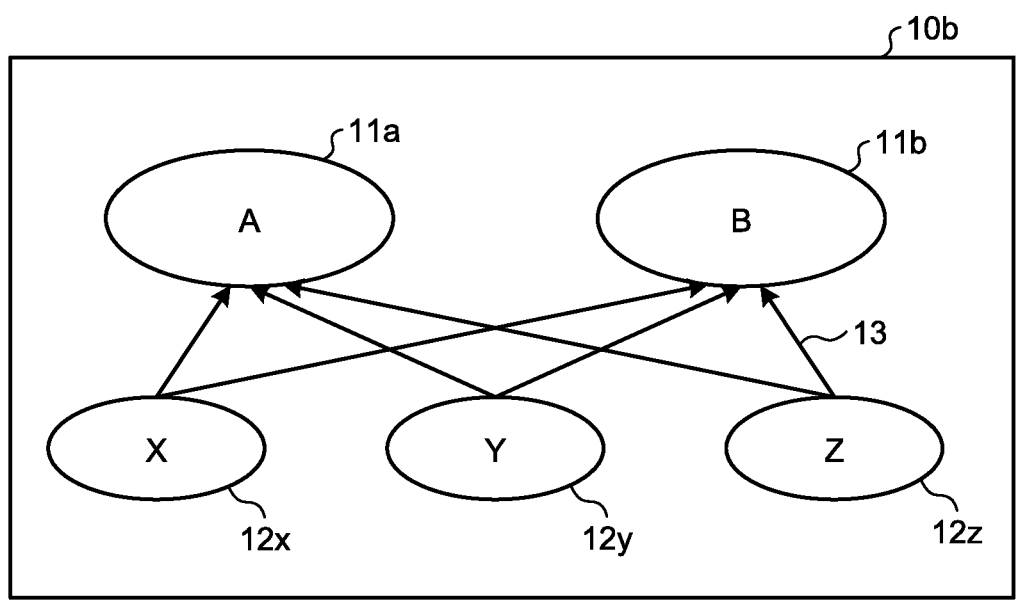
FIG. 2 is a diagram that illustrates an example of a complete bipartite graph according to a first embodiment.

Preferred embodiments will be explained with reference to accompanying drawings. Furthermore, the present invention is not limited to the embodiments. Moreover, the embodiments described below may be combined as needed as long as consistency is ensured.

[a] First Embodiment

First, a generation device 200 described later in the present embodiment reads a bipartite graph in which a node included in a first set and a node included in a second set are coupled to each other with an edge. The bipartite graph is used for, for example, machine learning processing on graph data. Sometimes, a node included in the first set is simply referred to as "the first node" below, and a node included in the second set is simply referred to as "the second node". Furthermore, "the first node" is an example of reference target data, and "the second node" is an example of reference source data. Moreover, the bipartite graph according to the present embodiment may be a directed graph or a non-directed graph.

According to the present embodiment, the first node corresponds to, for example, a domain present in a protein or a gene region in a genome sequence, and the second node corresponds to, for example, information on amino acid substitution or information on a base variant. Furthermore, the information that corresponds to the first node and the second node in the bipartite graph is an example, and the bipartite graph may be such that, for example, the first node corresponds to a gene region in a genome sequence and the second node corresponds to information on a base variant.

With reference to FIG. 1, an explanation is given of a bipartite graph and information that corresponds to each node according to the present embodiment. FIG. 1 is a diagram that illustrates an example of the relationship between a gene region in a genome sequence and a variant of a base. In FIG. 1, a gene A and a gene B are present in a genome sequence GN. Furthermore, a variant V and a variant X are present in the region of the gene A, and a variant Y is present in the region of the gene B.

In this case, a bipartite graph 10a may be represented, in which the gene A and the gene B are the first nodes and the variant V, the variant X, and the variant Y are the second nodes. In the bipartite graph 10a, the gene A is connected to the variant V present in the region of the gene A with an edge 13a and is connected to the variant X with an edge 13b. Similarly, the gene B is connected to the variant Y present in the region of the gene B with an edge 13c.

Furthermore, the relationship illustrated in the bipartite graph 10a may be represented by a table 14. The table 14 stores a gene and a variant included in the gene in a related manner.

Furthermore, when the number of nodes included in the bipartite graph increases, a complete bipartite graph is sometimes formed in which, for example, the second node corresponding to a certain first node and the second node corresponding to another first node are overlapped. According to the present embodiment, the complete bipartite graph is a bipartite graph in which the first node is connected to every second node with a single edge and the second node is connected to every first node with a single edge.

Furthermore, the generation device 200 extracts a complete bipartite graph from the read bipartite graph. FIG. 2 is a diagram that illustrates an example of the complete bipartite graph according to the first embodiment. As illustrated in FIG. 2, first nodes 11a and 11b in a complete bipartite graph 10b are connected to every one of second nodes 12x, 12y, and 12z included in the complete bipartite graph 10b with a single edge 13. That is, the second nodes 12x, 12y, and 12z in the complete bipartite graph 10b are also connected to every one of the first nodes 11a and 11b included in the complete bipartite graph 10b with the single edge 13.

Figure 3:
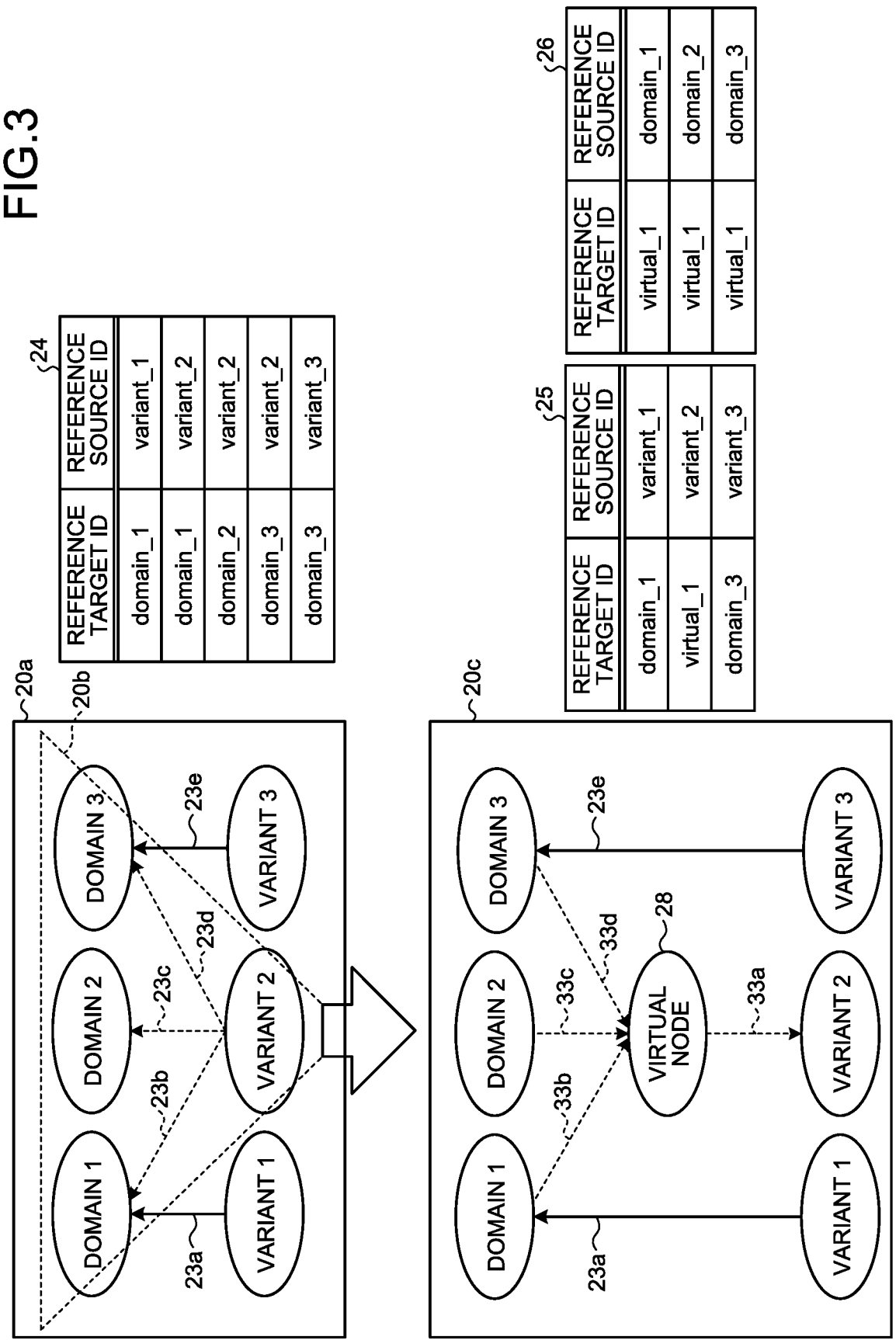
FIG. 3 is a diagram that illustrates an example of overlapped-region generation processing according to a typical technology.

Then, for example, the generation device 200 generates a virtual node that corresponds to the extracted complete bipartite graph to reduce the number of edges included in the bipartite graph. However, generation of a virtual node sometimes increases the number of edges to the contrary. FIG. 3 is a diagram that illustrates an example of overlapped-region generation processing according to a typical technology. A table 24 illustrated in FIG. 3 stores "reference target ID (Identifier)" and "reference source ID" in a related manner. In the table 24, the identifier for uniquely identifying information that corresponds to reference target data, such as a gene region included in a genome sequence, is stored as "reference target ID". Moreover, the identifier for uniquely identifying, for example, a variant of a base included in a genome sequence is stored as "reference source ID".

The relationship illustrated in the table 24 of FIG. 3 may be represented as a bipartite graph 20a. The bipartite graph 20a includes three first nodes "domain 1" to "domain 3", three second nodes "variant 1" to "variant 3", and five edges 23a to 23e. In the bipartite graph 20a, for example, the first node "domain 1" corresponds to the reference target ID "domein_1" in the table 24, and the second node "variant 1" corresponds to the reference source ID "variant_1". Moreover, the five edges 23a to 23e correspond to respective records in the table 24.

In the bipartite graph 20a, the variant 2 is connected to all the domains 1 to 3 included in the bipartite graph 20a with the edges 23b, 23c, and 23d, respectively. That is, all the domains 1 to 3 included in the bipartite graph 20a are connected to the variant 2 with the edges 23b, 23c, and 23d, respectively. In this case, the domains 1 to 3 and the variant 2 form a complete bipartite graph 20b.

By generating a virtual node 28 that corresponds to the complete bipartite graph 20b, the bipartite graph 20a is converted into a graph 20c. However, in the graph 20c, as illustrated in tables 25 and 26 of FIG. 3, replacement of the edges 23b to 23d by edges 33a to 33d and also addition of the new edge 33a cause an increase in the number of edges to six.

Therefore, the generation device 200 according to the present embodiment generates a virtual node that corresponds to a complete bipartite graph part when there are multiple sets of reference source data and multiple sets of reference target data in a complete bipartite graph included in the bipartite graph. Conversely, the generation device 200 refrains from generating a virtual node when at least any of the number of sets of reference source data and the number of sets of reference target data in the complete bipartite graph is one.

Furthermore, the generation device 200 may generate a virtual node that corresponds to a complete bipartite graph part when the total number of sets of reference source data and sets of reference target data in the complete bipartite graph included in the bipartite graph is equal to or more than six and when there are multiple sets of reference source data and multiple sets of reference target data in the complete bipartite graph included in the bipartite graph.

Figure 4:
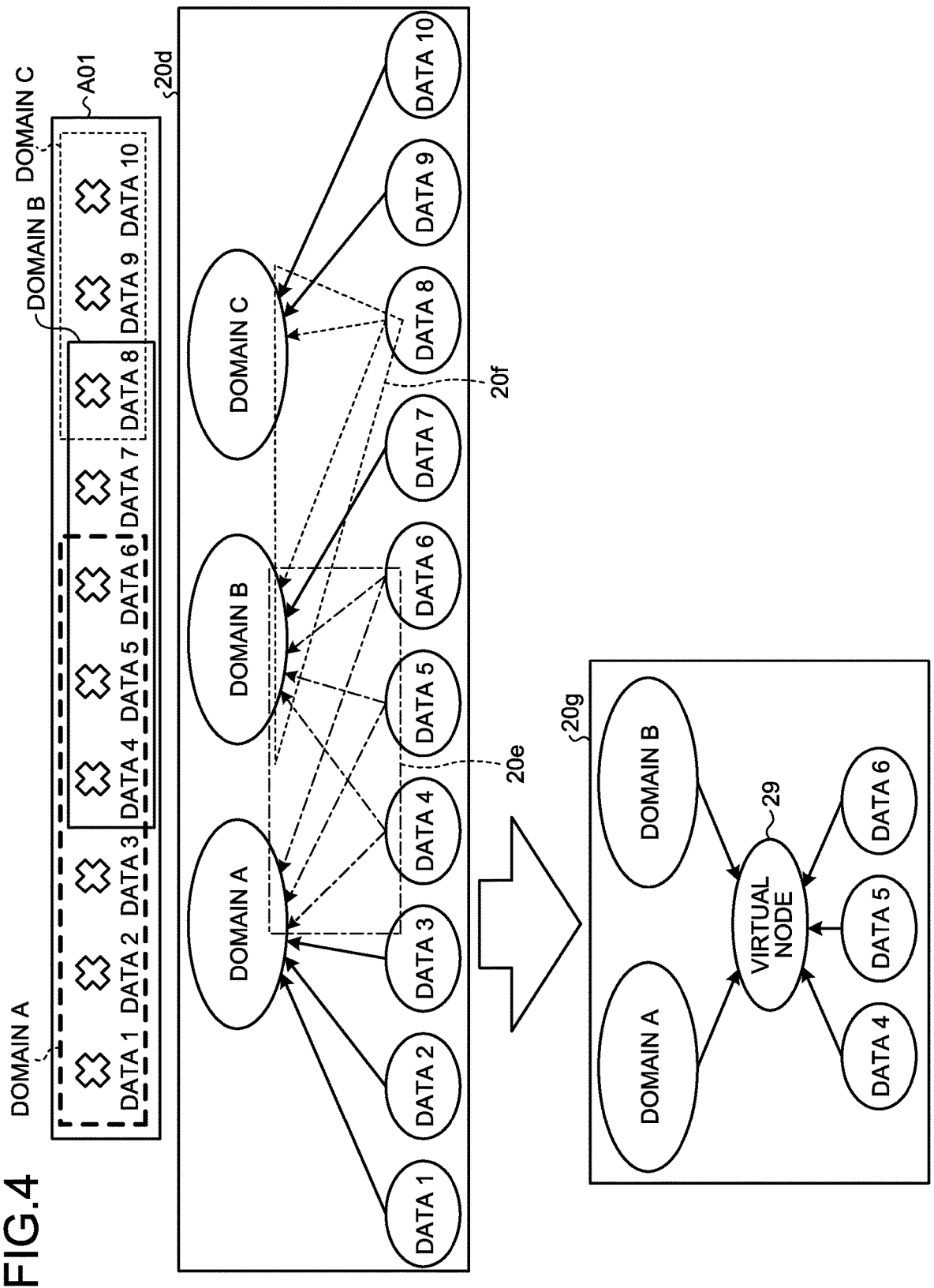
FIG. 4 is a diagram that illustrates an example of virtual-node generation processing according to the first embodiment.

FIG. 4 is a diagram that illustrates an example of virtual-node generation processing according to the first embodiment. In FIG. 4, a region A01 includes domains from a domain A to a domain C and includes data 1 to data 10. In FIG. 4, the domain A includes the data 1 to the data 6. Similarly, the domain B includes the data 4 to the data 8, and the domain C includes the data 8 to the data 10.

The relationship between the domain A to the domain C as the first nodes and the data 1 to the data 10 as the second nodes may be represented as a bipartite graph 20d. The bipartite graph 20d includes 3 first nodes, 10 second nodes, and 14 edges.

In FIG. 4, the domain A and the domain B include the data 4 to the data 6 in common. That is, the domain A, the domain B, and the data 4 to the data 6 form a complete bipartite graph 20e. In the same manner, as the domain B and the domain C include the data 8 in common, the domain B, the domain C, and the data 8 form a complete bipartite graph 20f.

In this case, the generation device 200 according to the present embodiment generates a virtual node 29 that corresponds to the complete bipartite graph 20e in which there are multiple first nodes and multiple second nodes, thereby converting the complete bipartite graph 20e into a graph 20g. Conversely, the generation device 200 according to the present embodiment refrains from generating a virtual node that corresponds to the complete bipartite graph 20f in which there is one second node.

Figure 5:
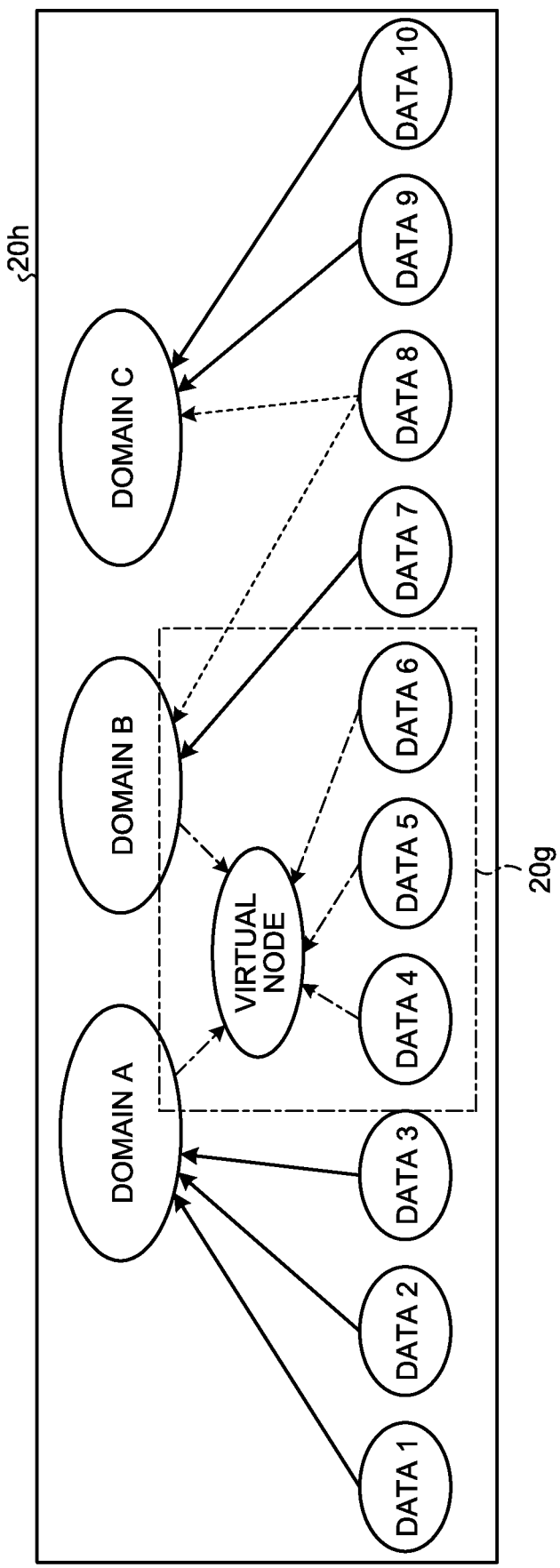
FIG. 5 is a diagram that illustrates an example of a virtual-node generation result according to the first embodiment.

FIG. 5 is a diagram that illustrates an example of a virtual-node generation result according to the first embodiment. A graph 20h illustrated in FIG. 5 includes 3 first nodes, 10 second nodes, and 1 virtual node. Furthermore, the number of edges included in the graph 20h is 13, and it is reduced as compared with the bipartite graph 20d.

In this way, the generation device 200 according to the present embodiment generates a virtual node that corresponds to a complete bipartite graph part when there are multiple reference sources and multiple reference targets in a complete bipartite graph included in the bipartite graph, whereby the amount of data representing a graph used for learning processing may be suppressed.

Functional Block

Figure 6:
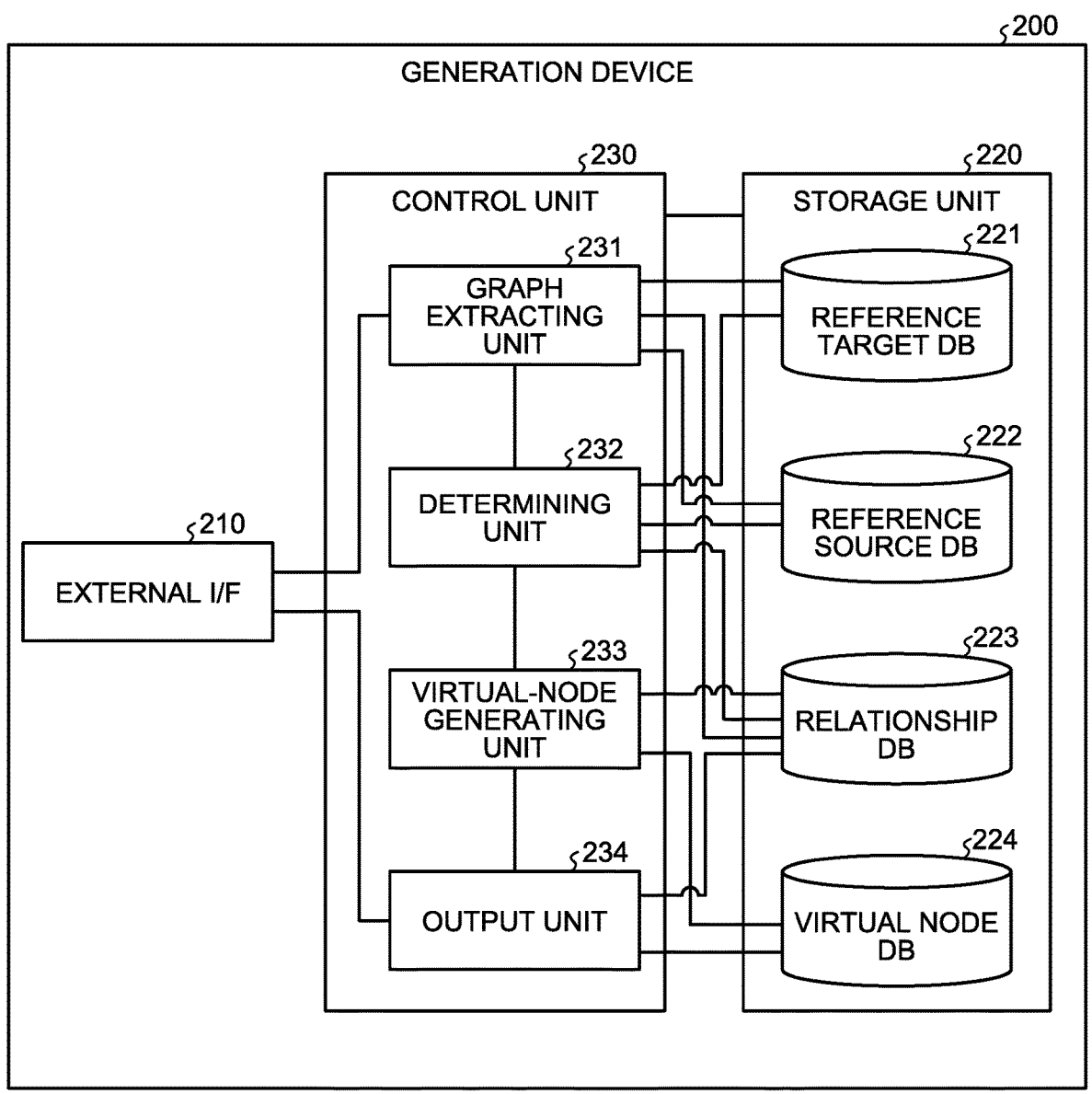
FIG. 6 is a diagram that illustrates an example of a generation device according to the first embodiment.

Next, the generation device 200 according to the present embodiment is explained with reference to FIG. 6. FIG. 6 is a diagram that illustrates an example of the generation device according to the first embodiment. The generation device 200 according to the present embodiment includes an external I/F (Interface) 210, a storage unit 220, and a control unit 230.

The external I/F 210 controls input/output and communications with other computers, such as a terminal (not illustrated) of a user (not illustrated) who uses the generation device 200 regardless of whether it is wired or wireless. The external I/F 210 is a communication interface, such as NIC (Network Interface Card); however, this is not a limitation, and it may be composed of an input device, such as keyboard, or an output device, such as display.

The storage unit 220 is an example of a storage device that stores, for example, various types of data such as programs executed by the control unit 230, and it is for instance a memory or a processor. The storage unit 220 includes a reference target DB 221, a reference source DB 222, a relationship DB 223, and a virtual node DB 224. Furthermore, in the following explanation, a database is sometimes referred to as "DB".

The reference target DB 221 stores information about the first node that is the reference target in a bipartite graph, such as a domain of a protein or a gene region in a genome sequence. FIG. 7 is a diagram that illustrates an example of the reference target DB according to the first embodiment. As illustrated in FIG. 7, the reference target DB 221 stores, for example, "protein ID", "start position", "end position", and "domain ID" by being related to "reference target ID". Furthermore, information stored in the reference target DB 221 is input by, for example, a graph extracting unit 231, described later. The reference target DB 221 stores, for example, one record for each reference target.

In FIG. 7, "reference target ID" indicates the information for uniquely identifying the first node that corresponds to, for example, a domain included in a protein. "Protein ID" indicates the information for uniquely identifying the protein in which the domain is included. "Start position" and "end position" indicate the coordinate at which the domain starts and the coordinate at which it ends. "Domain ID" indicates the information for uniquely identifying the domain.

Then, the reference source DB 222 stores information about the second node that is the reference source in a bipartite graph, such as amino acid substitution included in a protein or a variant of a base included in a genome sequence. FIG. 8 is a diagram that illustrates an example of the reference source DB according to the first embodiment. As illustrated in FIG. 8, the reference source DB 222 stores, for example, "coordinate" by being related to "reference source ID". Furthermore, information stored in the reference source DB 222 is input by, for example, the graph extracting unit 231. For example, the reference source DB 222 stores one record for each variant.

In FIG. 8, "reference source ID" indicates the information for uniquely identifying the second node that corresponds to for example amino acid substitution included in a protein. "Coordinate" indicates the coordinate at which the amino acid substitution is present.

Then, the relationship DB 223 stores the correspondence relationship between reference target data and reference source data. FIG. 9 is a diagram that illustrates an example of the relationship DB according to the first embodiment. As illustrated in FIG. 9, the relationship DB 223 stores for example "reference target ID" and "reference source ID" in a related manner. Furthermore, the information stored in the relationship DB 223 is input by, for example, the graph extracting unit 231 and is then updated by a virtual-node generating unit 233 described later. For example, the relationship DB 223 stores one record for each correspondence relationship between reference target ID and reference source ID. Specifically, when one reference target ID is related to two reference source IDs, the relationship DB 223 stores two records for the reference source ID. Furthermore, one record in the relationship DB 223 corresponds to one edge.

In FIG. 9, the reference source ID represents reference source data that is related to the reference target ID. For example, the reference target ID "A" is related to 6 sets of reference source data from the reference source ID "1" to "6". In the same manner, for example, the reference target ID "B" is related to 5 sets of reference source data from the reference source ID "4" to "8".

In this case, each of the first nodes that correspond to the reference target IDs "A" and "B" included in a region 223x is connected to each of the second nodes that correspond to all the reference source IDs "4" to "6" included in the region 223x with a single edge. That is, each of the second nodes that correspond to the reference source IDs "4" to "6" included in the region 223x is connected to each of the first nodes that correspond to all the reference target IDs "A" and "B" included in the region 223x with a single edge. Thus, the first nodes that correspond to the reference target IDs "A" and "B" and the second nodes that correspond to the reference source IDs "4" to "6" form a complete bipartite graph. Similarly, the first nodes that correspond to the reference target IDs "B" and "C" included in a region 223z and the second node that corresponds to the reference source ID "8" form a complete bipartite graph.

Then, the virtual node DB 224 stores information about a virtual node that is generated corresponding to a complete bipartite graph. FIG. 10 is a diagram that illustrates an example of the virtual node DB according to the first embodiment. As illustrated in FIG. 10, the virtual node DB 224 stores "reference target ID" by being related to "virtual node ID". Furthermore, the information stored in the virtual node DB 224 is input by, for example, the virtual-node generating unit 233.

In FIG. 10, "virtual node ID" indicates the information for uniquely identifying the virtual node that corresponds to a complete bipartite graph. "Reference target ID" uniquely identifies the first node related to the virtual node. FIG. 10 is an example of records related to the virtual node that corresponds to the complete bipartite graph formed by the first nodes that correspond to the reference target IDs "A" and "B" and the second nodes that correspond to the reference source IDs "4" to "6" included in for example the region 223x of FIG. 9. As illustrated in FIG. 10, the virtual node DB 224 stores for example one record for each correspondence relationship between the virtual node and the first node. Specifically, when one virtual node is related to two first nodes, the virtual node DB 224 stores two records for the reference target IDs of the first nodes. Furthermore, one record in the virtual node DB 224 corresponds to one edge.

With reference back to FIG. 6, the control unit 230 is a processing unit that controls the entire generation device 200, and it is for example a processor. The control unit 230 includes the graph extracting unit 231, a determining unit 232, the virtual-node generating unit 233, and an output unit 234. Furthermore, the graph extracting unit 231, the determining unit 232, the virtual-node generating unit 233, and the output unit 234 are examples of an electronic circuit included in the processor or examples of a process executed by the processor.

The graph extracting unit 231 extracts a part that forms a complete bipartite graph from data on the bipartite graph. For example, the graph extracting unit 231 receives a command to start to generate data including data on a bipartite graph from the terminal of the user who uses the generation device 200 via the external I/F 210. The graph extracting unit 231 extracts the information about reference target data on a gene region or a domain of a protein from data on the bipartite graph included in the start command, applies a reference target ID to it, and stores it in the reference target DB 221. Similarly, the graph extracting unit 231 extracts information about reference source data on gene variant, amino acid substitution, or the like, from data on the bipartite graph, applies a reference target ID to it, and stores it in the reference source DB 222. Furthermore, the graph extracting unit 231 extracts a part that forms a complete bipartite graph and outputs it to the determining unit 232.

The determining unit 232 determines whether the virtual node that corresponds to the extracted complete bipartite graph is generated. For example, the determining unit 232 determines whether the number of edges included in the bipartite graph may be reduced by generating the virtual node that corresponds to the complete bipartite graph.

For example, the determining unit 232 determines whether the complete bipartite graph contains multiple reference target nodes and multiple reference source nodes. The determining unit 232 outputs, to the virtual-node generating unit 233, information about the complete bipartite graph for which it is determined that there are multiple reference target nodes and multiple reference source nodes. The determining unit 232 refrains from outputting information about the complete bipartite graph when it is determined that at least any of the reference target node and the reference source node is not more than one.

Furthermore, the determining unit 232 may determine whether the total number of reference target nodes and reference source nodes included in the complete bipartite graph is equal to or more than six. Here, the determining unit 232 outputs, to the virtual-node generating unit 233, information about the complete bipartite graph for which it is determined that the total number of reference target nodes and reference source nodes is equal to or more than six and there are multiple sets of reference source data and multiple sets of reference target data in the complete bipartite graph included in the bipartite graph. The determining unit 232 refrains from outputting information about the complete bipartite graph when it is determined that the total number of reference target nodes and reference source nodes is equal to or more than six and that there are not multiple sets of reference source data or multiple sets of reference target data in the complete bipartite graph included in the bipartite graph.

FIG. 11 is a diagram that illustrates an example of data used during a virtual-node determination process according to the first embodiment. As illustrated in FIG. 11, the determining unit 232 generates a virtual node ID by being related to the complete bipartite graph for which it is determined that the corresponding virtual node is generated. According to the present embodiment, for example, the determining unit 232 generates a virtual node ID only when the complete bipartite graph contains multiple reference target nodes and multiple reference source nodes.

For example, the determining unit 232 generates a virtual node ID "VI" by being related to the complete bipartite graph including the first nodes that corresponds to the reference target IDs "A" and "B" and the second nodes that correspond to the reference source IDs "4" to "6". Conversely, the determining unit 232 does not generate a virtual node ID for the complete bipartite graph including the first nodes that correspond to the reference target IDs "B" and "C" and the second node that corresponds to the reference source ID "8". Then, the determining unit 232 outputs the generated virtual node ID "VI" and information about the corresponding complete bipartite graph to the virtual-node generating unit 233.

The virtual-node generating unit 233 converts the complete bipartite graph into the graph including the corresponding virtual node. After the virtual node ID and information about the corresponding complete bipartite graph are input from the determining unit 232, the virtual-node generating unit 233 stores information about the virtual node that corresponds to the complete bipartite graph in the virtual node DB 224.

Furthermore, the virtual-node generating unit 233 uses the information about the virtual node to update the relationship DB 223 illustrated in FIG. 9. FIG. 12 is a diagram that illustrates an example of the relationship DB after a virtual node is generated according to the first embodiment. As illustrated in FIG. 12, the virtual-node generating unit 233 updates the region 223$x$ in the relationship DB 223 illustrated in FIG. 9 by using the output virtual node ID "VI" so as to represent a region 223$y$. Conversely, the virtual-node generating unit 233 does not update a region 223$z$ in the relationship DB 223 as no virtual node ID is output.

The output unit 234 outputs information about a graph including the graph that is converted from the complete bipartite graph by using the corresponding virtual node. The output unit 234 generates the graph 20$h$ illustrated in FIG. 5 by referring to for example the updated relationship DB 223 illustrated in FIG. 12 and the virtual node DB 224. Then, the output unit 234 outputs the generated graph 20$h$ to the terminal of the user who uses the generation device 200 via the external I/F 210.

Flow of Process

Figure 13:
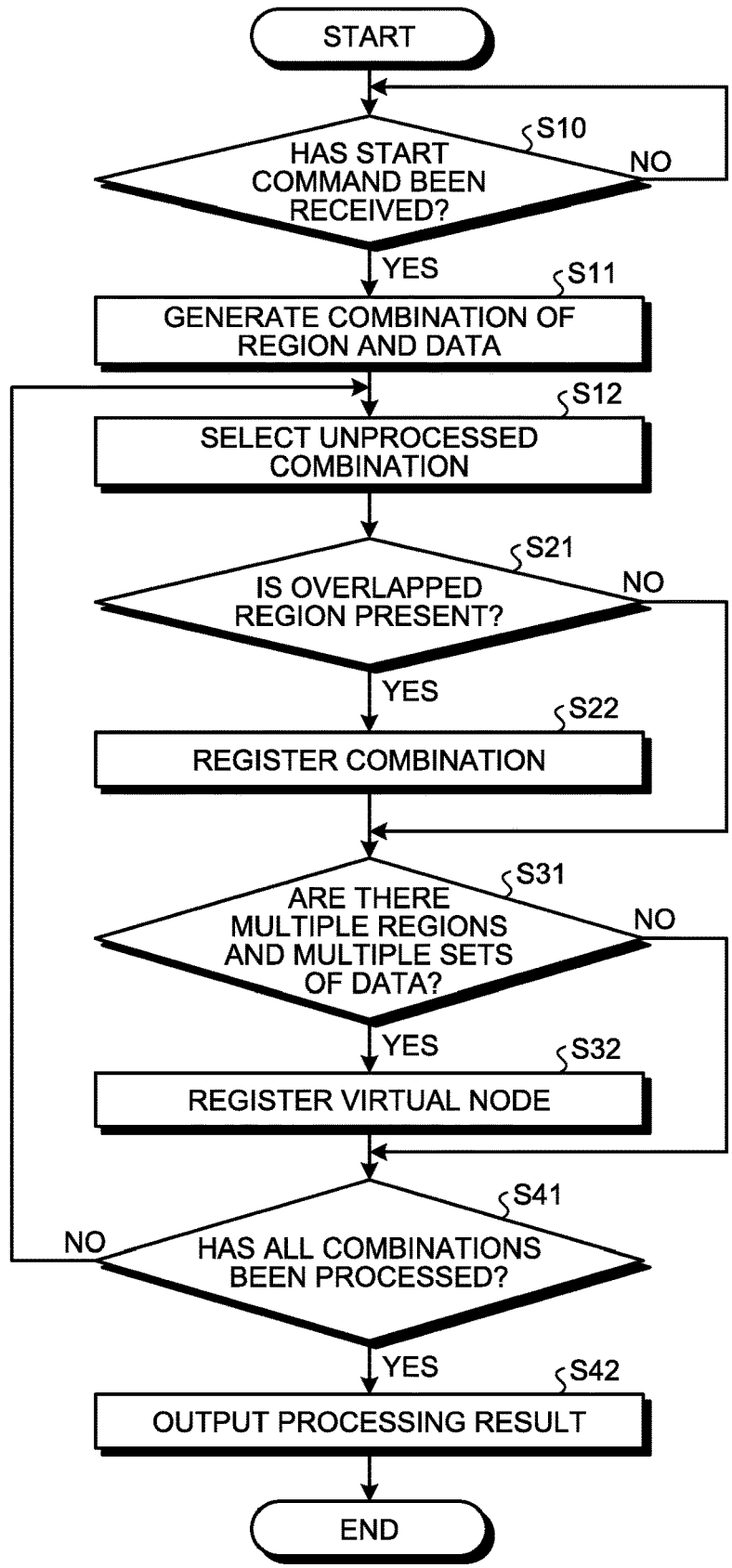
FIG. 13 is a flowchart that illustrates an example of a generation process according to the first embodiment.

Next, a process according to the present embodiment is explained with reference to FIG. 13. FIG. 13 is a flowchart that illustrates an example of a generation process according to the first embodiment. As illustrated in FIG. 13, the graph extracting unit 231 of the generation device 200 stands by until a command to start to generate data including data on the bipartite graph is received from the terminal of the user who uses the generation device 200 via for example the external I/F 210 (S10: No).

When it is determined that the command to start to generate data has been received (S10: Yes), the graph extracting unit 231 generates a combination of a region and data from data on the bipartite graph and stores it in the relationship DB 223 as illustrated in FIG. 9 (S11).

Then, the determining unit 232 selects an unprocessed combination from the combinations of a region and data stored in the relationship DB 223 (S12). For example, the combination of the first node that is the reference target ID "A" illustrated in FIG. 9 and the corresponding reference source IDs "1" to "6" is selected.

Then, the determining unit 232 determines whether a region is overlapped between the combination and a different combination (S21). When it is determined that there is an overlapped region (321: Yes), the determining unit 232 registers the combination and the different combination having the overlapped region as a virtual node candidate in the storage unit 220 (S22) and shifts to S31. Conversely, when it is determined that there is no overlapped region (S21: No), the determining unit 232 shifts to S31 without registering a virtual node candidate.

Then, the determining unit 232 determines whether there are multiple regions and multiple sets of data with regard to a virtual node candidate registered in the storage unit 220 (S31). When it is determined that there are multiple regions and multiple sets of data (S31: Yes), the determining unit 232 generates the virtual node ID that corresponds to the virtual node candidate. Then, the virtual-node generating unit 233 registers the information that corresponds to the virtual node ID in the virtual node DB 224, updates the relationship DB 223 (S32), and shifts to S41. Conversely, when it is determined that at least any of the region and the data is not more than one (S31: No), the determining unit 232 does not register information that corresponds to the virtual node ID, and it shifts to S41.

Then, the determining unit 232 returns to S12 and repeatedly performs the process until the process has been completed for all the combinations of a region and data (S41: No). Conversely, when the process has been completed for all the combinations of a region and data (S41: Yes), the output unit 234 outputs a processing result (S42) and terminates the process.

Advantage

As described above, the data structure according to the present embodiment is generated from the target in which multiple sets of reference source data and reference target data are connected by using edges. The data structure is generated by creating a virtual node between reference source data and reference target data when there are multiple sets of reference source data and multiple sets of reference target data that constitute a complete bipartite graph extracted from the connected target. The data structure is used by a learning device for a process to learn the relationship among reference source data, reference target data, and a virtual node. Thus, the generation device may reduce the amount of data representing a correspondence relationship used for machine learning processing.

Figure 14:
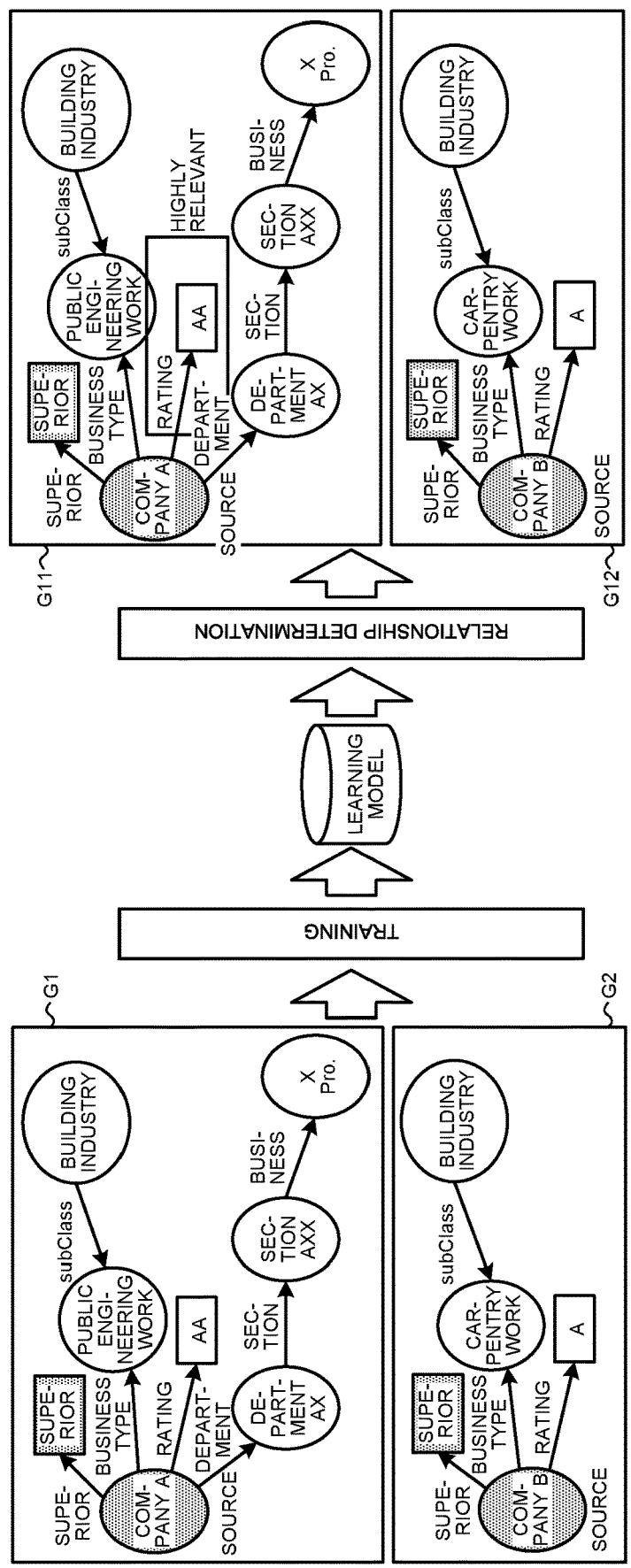
FIG. 14 is a diagram that illustrates an example of machine learning processing according to the first embodiment.

With reference to FIG. 14, an explanation is given of machine learning processing using a data structure generated according to the present embodiment. FIG. 14 is a diagram that illustrates an example of machine learning processing according to the first embodiment. The machine learning processing according to the present embodiment uses a technique for analyzing series data, such as RNN (Recurrent Neural Network). Furthermore, the machine learning processing may also use other neural networks, such as CNN (Convolutional Neural Network).

The learning illustrated in FIG. 14 includes a neural network. The neural network is composed of three layers, i.e., an input layer, an intermediate layer, and an output layer. Each layer is composed of one or more neurons. Furthermore, a neuron in each layer is connected to at least one neuron in a different layer. Specifically, a neuron in the input layer is connected to at least one neuron in the intermediate layer, and a neuron in the intermediate layer is connected to at least one neuron in the output layer. Furthermore, during back propagation processing, the relationship among reference source data, reference target data, and a virtual node is input, the output result corresponding to the input from the neural network is compared with the supervised data that corresponds to the relationship, and weights are updated in sequence from a layer (intermediate layer) close to the output layer of the neural network to the input layer so as to reduce an error in the two sets of data. That is, weights in the input data are updated in the direction opposite to the output direction. For example, the relationship among reference source data, reference target data, and a virtual node corresponds to susceptibility to a specific disease or resistance to a side effect of a medicine. Moreover, the supervised data is information about susceptibility to a specific disease or resistance to a side effect of a medicine.

In FIG. 14, graphs G1 and G2 are graph data used for machine learning processing. During the machine learning processing according to the present embodiment, for example, supervised data is generated to make a classification as to what kind of relationship is present among "company A", which is reference source data in the graph G1, department "department AX" and rating "AA", which are reference target data, and the like.

In these graphs, for example, when there is a complete bipartite graph that is common to the graphs G1 and G2, the data structure generated according to the first or the second embodiment is used to reduce the amount of data used for machine learning processing.

Furthermore, during the machine learning processing according to the present embodiment, a trained model is generated by using the generated supervised data, and a process is performed to determine the relationship by using the trained model. Graphs G11 and G12 are results of the process to determine the relationship with the posed problem by using the graphs G1 and G2. As a result of the determination process, it is determined that, in the graph G11, rating "AA" is highly relevant to the posed problem, that is, it is useful to estimate determination. Conversely, in the graph G12, there is no reference target data that is determined to be highly relevant to the posed problem. In such a case, a weight to a parameter in the trained model may be updated with regard to the correspondence relationship that is useful to estimate determination.

Furthermore, when a data structure according to the present embodiment is generated, it may be determined whether there are multiple sets of reference target data with respect to reference source data included in the complete bipartite graph and whether there are multiple sets of reference source data with respect to reference target data. For generation of a data structure, when it is determined that, with respect to at least any one of reference source data and reference target data, another one of them is one in number, the edge connecting the reference source data and the reference target data may be retained without generating a virtual node. Thus, the amount of data may be reduced more effectively.

Furthermore, in the data structure according to the present embodiment, information relating reference source data and reference target data may be replaced with information relating reference source data and a virtual node and information relating reference target data and a virtual node. Thus, a graph including a virtual node may be easily generated.

Furthermore, in a complete bipartite graph extracted when a data structure is generated according to the present embodiment, each set of reference source data is connected to every set of reference target data with a single edge and each set of reference target data is connected to every set of reference source data with a single edge. Thus, a new graph may be generated without missing or overlapped information.

Furthermore, a complete bipartite graph may be extracted in which a domain of a protein or a gene region in a genome sequence are reference target data and information about amino acid substitution or information about a variant of a base are reference source data. Thus, the amount of data representing a graph regarding a protein or a gene may be reduced.

[b] Second Embodiment

Furthermore, when regions are overlapped with regard to a gene region, a domain of a protein, or the like, a complete bipartite graph is generated. In this case, the range of the region or the position of a variant or substitution is representable with a coordinate; therefore, the presence or absence of a complete bipartite graph may be determined by comparing coordinates.

Figure 15:
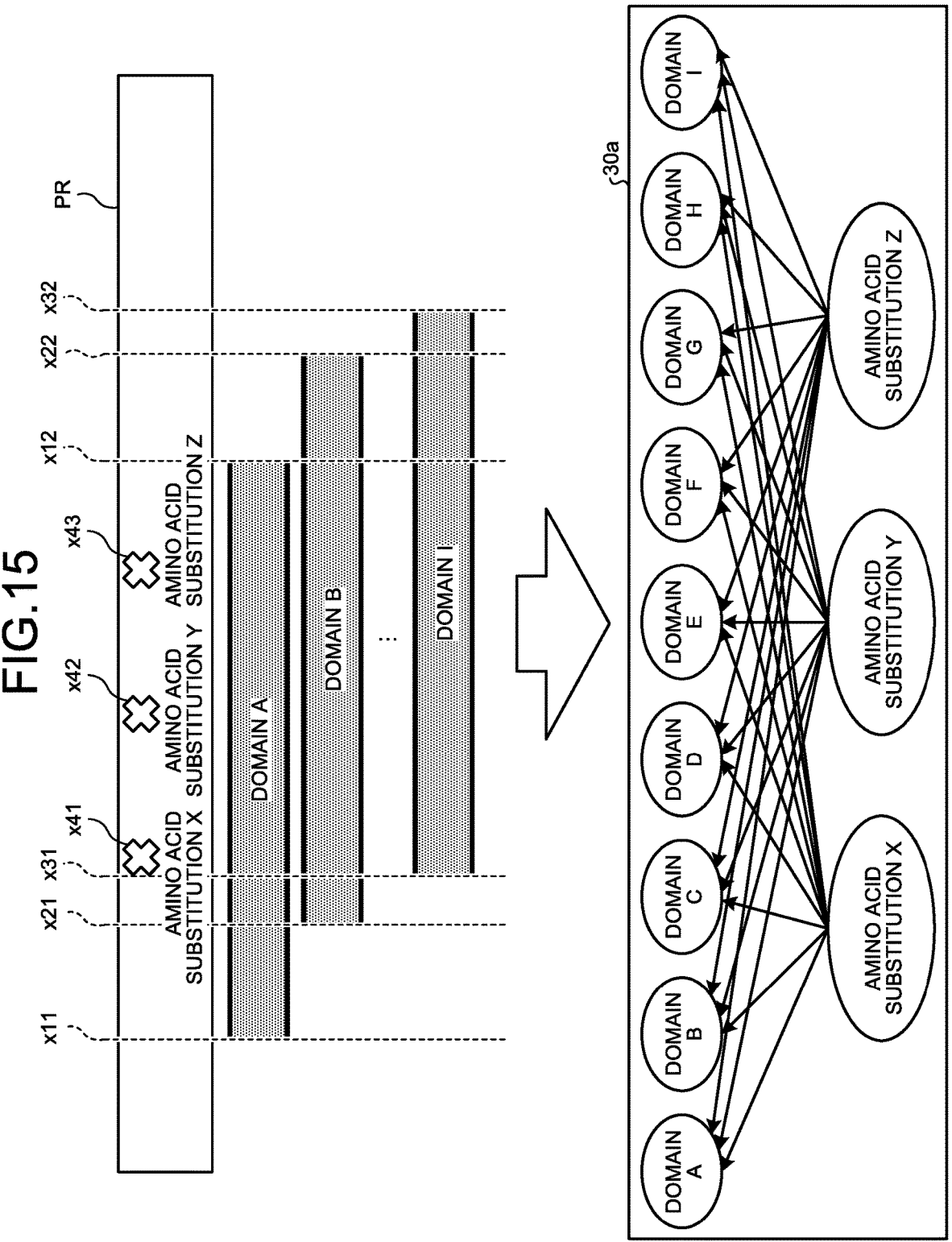
FIG. 15 is a diagram that illustrates an example of the relationship between a domain of a protein and amino acid substitution according to a second embodiment.

FIG. 15 is a diagram that illustrates an example of the relationship between a domain of a protein and amino acid substitution according to the second embodiment. As illustrated in FIG. 15, with regard to a protein PR, the start position of the domain A is a coordinate x11, and the end position thereof is a coordinate x12. Also, the start positions of the domain B and a domain I are a coordinate x21 and a coordinate x31, respectively, and the end positions thereof are a coordinate x22 and a coordinate x32, respectively. Furthermore, the positions of amino acid substitution X to amino acid substitution Z are a coordinate x41, a coordinate x42, and a coordinate x43, respectively. Here, the correspondence relationship among the domain A to the domain I and the amino acid substitution X to the amino acid substitution Z are represented by a bipartite graph 30a.

Furthermore, when it is determined whether regions are overlapped by using coordinates, it is possible that there are multiple combinations of regions that cause a complete bipartite graph. For example, in FIG. 15, although each of the domain A to the domain I is overlapped, the domain A and the domain B, the domain B and the domain I are also overlapped. In this case, a configuration may be such that the one with which the amount of data may be reduced most effectively is selected from the combinations of regions.

Therefore, in the present embodiment, an explanation is given of a configuration in which it is determined whether regions causing a complete bipartite graph are overlapped by using a coordinate and the corresponding virtual node is generated. Furthermore, a combination of regions overlapped with each other is sometimes simply referred to as "overlapped region". Moreover, according to the present embodiment, a case where regions are overlapped includes a case where regions are completely matched and a case where one region is included in the other region in addition to a case where only part of a region is overlapped.

Functional Block

Figure 16:
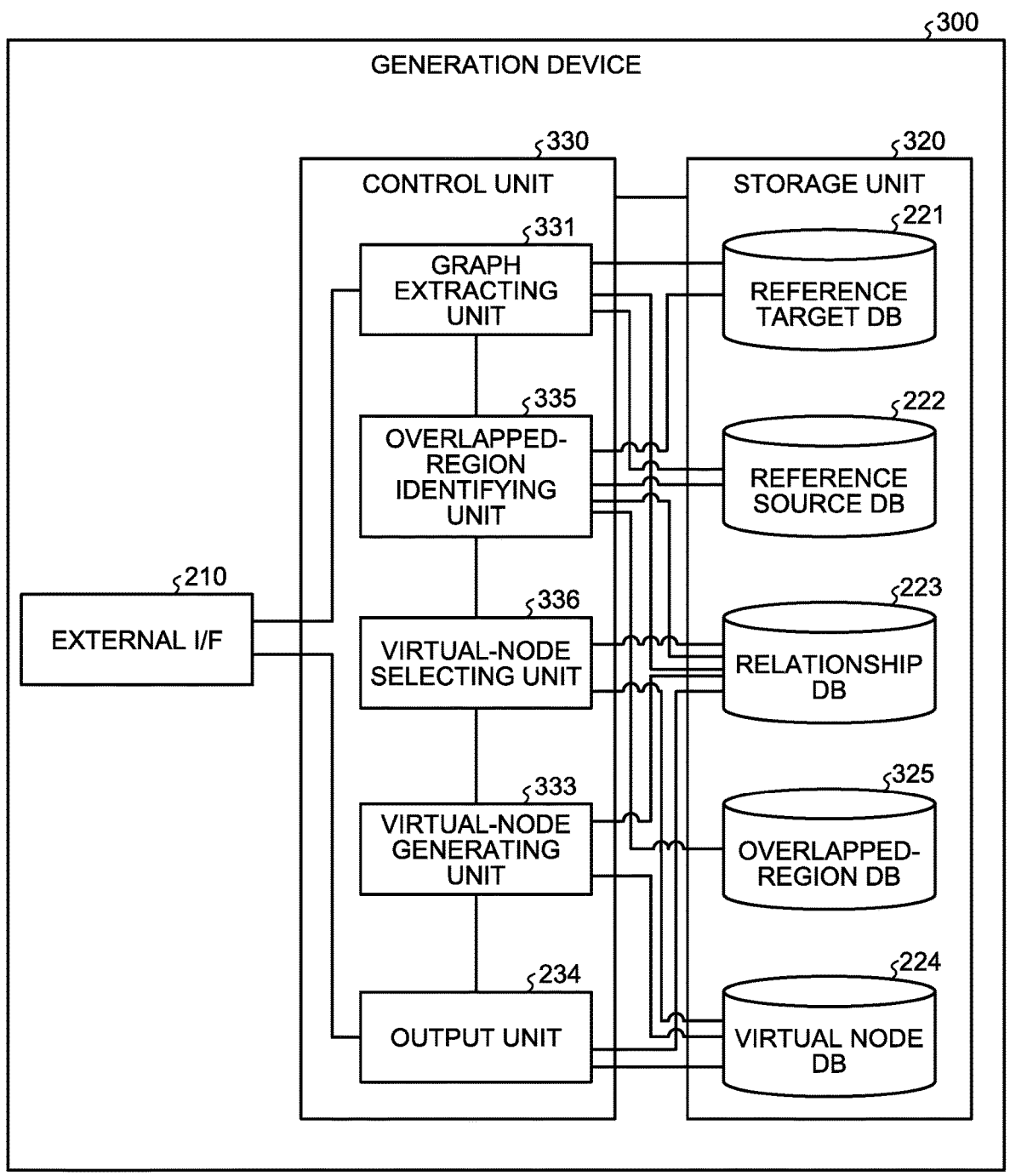
FIG. 16 is a diagram that illustrates an example of a generation device according to the second embodiment.

FIG. 16 is a diagram that illustrates an example of a generation device according to the second embodiment. Furthermore, in the following embodiment, the same component as that illustrated in the drawing described above is attached with the same reference numeral, and duplicated explanation is omitted.

As illustrated in FIG. 16, a generation device 300 according to the present embodiment includes the external I/F 210, a storage unit 320, and a control unit 330. The storage unit 320 is an example of a storage device that stores various types of data such as programs executed by for example the control unit 330, and it is for example a memory or a processor. Furthermore, the storage unit 320 includes the reference target DB 221, the reference source DB 222, the relationship DB 223, the virtual node DB 224, and an overlapped-region DB 325.

The overlapped-region DB 325 stores information about an overlapped region that is a candidate for a complete bipartite graph for which a virtual node is generated. FIG. 17 is a diagram that illustrates an example of the overlapped-region DB according to the second embodiment. As illustrated in FIG. 17, the overlapped-region DB 325 stores "protein ID", "combination of regions", "start position", and "end position" by being related to "overlapped region ID".

In FIG. 17, "overlapped region ID" indicates the information for uniquely identifying an overlapped region. "Combination of regions" indicates a combination of regions included in the overlapped region. "Start position" and "end position" indicate the coordinate of the start position and the coordinate of the end position of the part where the regions are overlapped.

Furthermore, as illustrated in a region 325x of FIG. 17, an overlapped region does not need to be the combination of successive regions but may be the one with a middle region excluded.

The control unit 330 is a processing unit that controls the entire generation device 300, and it is for example a processor. The control unit 330 includes a graph extracting unit 331, an overlapped-region identifying unit 335, a virtual-node selecting unit 336, a virtual-node generating unit 333, and the output unit 234. Furthermore, the graph extracting unit 331, the overlapped-region identifying unit 335, the virtual-node selecting unit 336, the virtual-node generating unit 333, and the output unit 234 are examples of an electronic circuit included in the processor or examples of a process executed by the processor.

The graph extracting unit 331 stores information about a bipartite graph in the reference target DB 221 and the reference source DB 222 in the same manner as the graph extracting unit 231 according to the first embodiment. However, the graph extracting unit 331 does not perform a process to extract a part that forms a complete bipartite graph.

The overlapped-region identifying unit 335 identifies multiple overlapped regions that form a complete bipartite graph from data on the bipartite graph. For example, the overlapped-region identifying unit 335 refers to the reference target DB 221 to extract multiple regions with the same protein ID (e.g., "P0XXX1").

Then, the overlapped-region identifying unit 335 determines whether the start position of the extracted region is present before the end position of another region. The overlapped-region identifying unit 335 stores, in the overlapped-region DB 325, the combination of regions for which it is determined that the start position of a region is present before the end position of another region.

For example, as the coordinate of the start position of the region with the reference target ID "A" is "5" and it is before the coordinate "132" of the end position of the region with the reference target ID "B", the overlapped-region identifying unit 335 stores the combination of the reference target IDs "A" and "B" in the overlapped-region DB 325. Furthermore, the overlapped-region identifying unit 335 repeatedly performs a process on all combinations of regions including, for example, combinations of three or more regions and combinations of regions with middle regions excluded.

From the overlapped regions, the virtual-node selecting unit 336 selects the one with which the amount of data is reduced most effectively. FIG. 18 is a diagram that illustrates an example of data used during a virtual-node selection process according to the second embodiment. For example, as illustrated in FIG. 18, the virtual-node selecting unit 336 refers to the overlapped-region DB 325, calculates the effect of reduction in the amount of data when the complete bipartite graph occurring in each overlapped region is converted into a virtual node, and stores it in the storage unit 320.

Furthermore, according to the present embodiment, the number obtained by subtracting the number of added edges from the number of reduced edges due to generation of a virtual node is used as the effect of reduction in the amount of data. The effect of reduction in the amount of data is calculated by using, for example, the following Equation that uses the number of sets of reference target data included in the complete bipartite graph and the number of sets of reference source data included in the complete bipartite graph.

Effect of reduction=number of sets of reference target data×number of sets of reference source data−(number of sets of reference target data+number of sets of reference source data)

For example, although the effect of reduction in the amount of data with the number of sets of reference source data "854" is "852" when the number of sets of reference target data is "2", it is "1705" when the number of sets of reference target data is "3". Similarly, for example, although the effect of reduction in the amount of data with the number of sets of reference source data "836" is "834" when the number of sets of reference target data is "2", it is "2504" when the number of sets of reference target data is "4".

Then, the virtual-node selecting unit 336 selects, from the records illustrated in FIG. 18, the one with the highest effect of reduction in the amount of data. For example, the virtual-node selecting unit 336 selects the overlapped region with the overlapped region ID "v19" whose effect of reduction is "2504". Then, the virtual-node selecting unit 336 outputs information about the selected overlapped region to the virtual-node generating unit 333. Furthermore, for example, when each of the overlapped regions independently generates a complete bipartite graph, the virtual-node selecting unit 336 may select multiple overlapped regions.

The virtual-node generating unit 333 generates a virtual node that corresponds to a complete bipartite graph generated from the overlapped region. After information about the overlapped region is input from the virtual-node selecting unit 336, the virtual-node generating unit 233 stores the information about the virtual node that corresponds to the complete bipartite graph generated from the overlapped region in the virtual node DB 224.

Flow of Process

Figure 19:
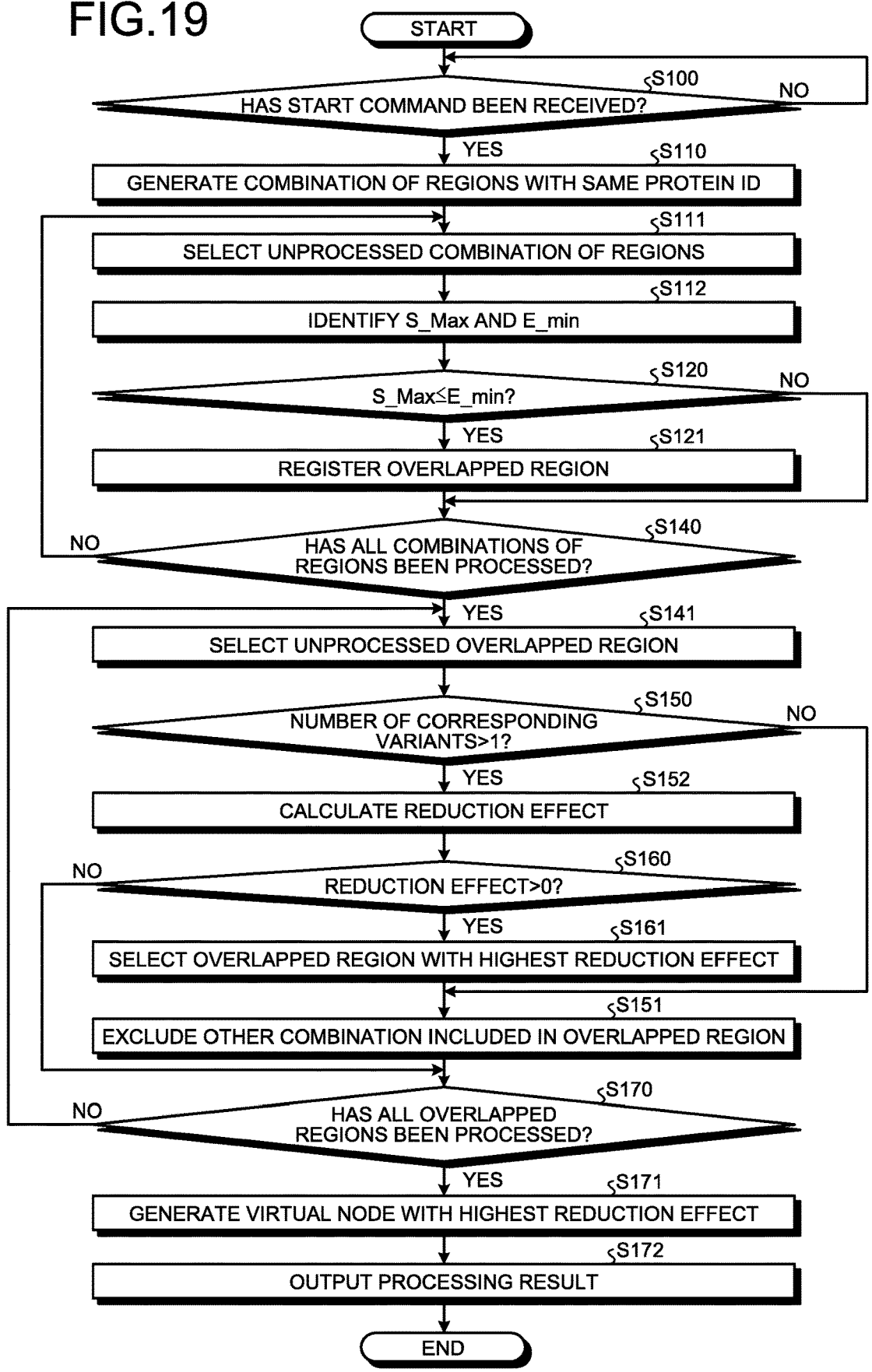
FIG. 19 is a flowchart that illustrates an example of a generation process according to the second embodiment.

Next, a process according to the present embodiment is explained with reference to FIG. 19. FIG. 19 is a flowchart that illustrates an example of a generation process according to the second embodiment. As illustrated in FIG. 19, the graph extracting unit 331 of the generation device 300 stands by until a command to start to generate data including data on a bipartite graph is received from the terminal of the user who uses the generation device 300 via for example the external I/F 210 (S100: No).

When it is determined that a command to start to generate data is received (S100: Yes), the graph extracting unit 331 generates a combination of a region and data from the data on the bipartite graph and stores it in the relationship DB 223 as illustrated in FIG. 9. Then, the overlapped-region identifying unit 335 generates a combination of regions with the same protein ID from the data on the bipartite graph (S110).

Then, the overlapped-region identifying unit 335 selects an unprocessed combination of regions from the generated combinations of regions (S111). For example, the combination of regions "A" and "C" corresponding to the overlapped region ID "v12" illustrated in FIG. 17 is selected.

Then, the overlapped-region identifying unit 335 identifies the maximum coordinate "S_Max" among the coordinates of the start positions of the regions included in the combination and the minimum coordinate "E_min" among the coordinates of the end positions of the regions included in the combination (S112). Then, the overlapped-region identifying unit 335 determines whether the ranges of the regions in the combination are overlapped, i.e., whether "S_Max" is equal to or less than "E_min" (S120).

When it is determined that the ranges are overlapped (S120: Yes), the overlapped-region identifying unit 335 registers the combination of regions as overlapped regions in the overlapped-region DB 325 (S121) and proceeds to S140.

Conversely, when it is determined that there is no overlapped region (S120: No), the overlapped-region identifying unit 335 proceeds to S140 without registering any overlapped region.

The overlapped-region identifying unit 335 returns to S111 and repeatedly performs the process until the process has been completed for all the combinations of regions (S140: No). When the process has been completed for all the combinations of regions (S140: Yes), the virtual-node selecting unit 336 refers to the overlapped-region DB 325 and selects an unprocessed overlapped region (S141).

Then, the virtual-node selecting unit 336 determines whether the number of variants corresponding to the unprocessed overlapped region is more than one (S150). When it is determined that the number of variants corresponding to the unprocessed overlapped region is not more than one (S150: No), the virtual-node selecting unit 336 excludes other overlapped regions that are entirely included in the overlapped region, stored in the overlapped-region DB 325, from the processed target (S151) and proceeds to S170.

Conversely, when it is determined that the number of variants corresponding to the unprocessed overlapped region is more than one (S150: Yes), the virtual-node selecting unit 336 calculates the effect of reduction in a case where the complete bipartite graph corresponding to the overlapped region is converted by using the corresponding virtual node (S152). Then, the virtual-node selecting unit 336 determines whether the effect of reduction is a positive number (S160). When it is determined that the effect of reduction is equal to or less than zero (S160: No), the virtual-node selecting unit 336 proceeds to S170.

Conversely, when it is determined that the effect of reduction is a positive number (S160: Yes), the virtual-node selecting unit 336 selects the one with the highest effect of reduction from the processed overlapped regions (S161) and then proceeds to S151.

Then, the virtual-node selecting unit 336 returns to S141 and repeatedly performs the process until the process has been completed for all the overlapped regions (S170: No). Conversely, when the process has been completed for all the overlapped regions (S170: Yes), the virtual-node generating unit 333 generates a virtual node that corresponds to the overlapped region with the highest effect of reduction (S171). Then, the output unit 234 outputs a processing result (S172) and terminates the process.

Advantage

As described above, according to the present embodiment, the generation device 300 may calculate the number of edges connecting reference source data and a virtual node and the number of edges connecting reference target data and a virtual node, the edges being generated when a virtual node is created. Furthermore, the generation device 300 may calculate the number of edges connecting reference source data and reference target data, the edges being reduced when the virtual node is created. Moreover, the generation device 300 may generate a virtual node with which the number obtained by subtracting the number of generated edges from the number of reduced edges is largest. Thus, a graph with the highest effect of reduction in the amount of data may be generated.

Furthermore, a complete bipartite graph may be extracted by using at least any of the coordinate specifying the start position and the coordinate specifying the end position of the region that corresponds to reference source data and the coordinate specifying the start position and the coordinate specifying the end position of the region that corresponds to reference target data. Thus, a graph with the amount of data reduced may be generated, targeted for a region identified with a coordinate. Furthermore, when three or more regions are extracted by using a coordinate, a part of the extracted regions may be excluded to generate a virtual node.

[c] Third Embodiment

Although the embodiments according to the present invention are explained above, the present invention may be implemented in various different embodiments other than the above-described embodiments.

Furthermore, the storage unit 220 may be configured to use a single table so as to collectively store information that is stored in each of the reference target DB 221, the reference source DB 222, the relationship DB 223, and the virtual node DB 224. In this case, the storage unit 220 may collectively store various types of information by using for example RDF (Resource Description Framework) file.

Figures 20, 21:
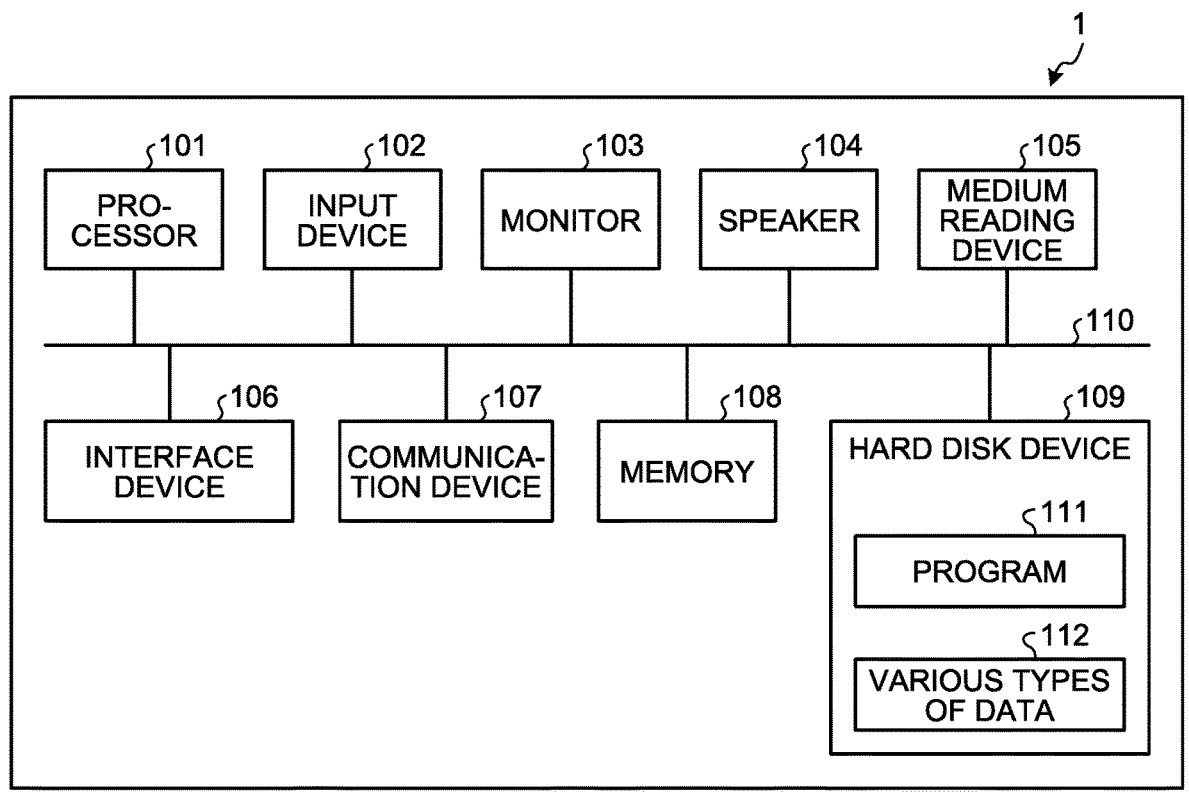
FIG. 20 is a diagram that illustrates an example of an RDF file.
FIG. 21 is a diagram that illustrates an example of a hardware configuration.

FIG. 20 is a diagram that illustrates an example of an RDF file. As illustrated in FIG. 20, the RDF file stores "s" (subject), "p" (property), and "o" (object) in a related manner.

In the RDF file of FIG. 20, the relationship between the subject and the object is represented by "property". For example, the RDF file stores that "start coordinate" of the region "A" is "4". Furthermore, the RDF file stores that the region "A" contains "1" that is "variant" and "coordinate" of the variant "1" is "4".

In this way, the data structure may further include information indicating the relationship between reference source data and a virtual node and information indicating the relationship between reference target data and a virtual node. Thus, multiple pieces of information are collected in a single table.

Furthermore, in the data structure generated according to each of the embodiments, the target complete bipartite graph to be converted may be a directed graph or a non-directed graph.

Furthermore, all or any part of various types of processing functions executed by the generation device 200 or 300 may be conducted by a processor. Moreover, it is obvious that all or any part of various processing functions may be executed by a program analyzed and executed by the processor or wired logic hardware.

Furthermore, various processes explained in the above embodiment may be performed when a prepared program is executed by a computer. Therefore, an explanation is given below of an example of the computer (hardware) that executes a program having the same functionality as that in the above embodiment. FIG. 21 is a diagram that illustrates an example of a hardware configuration. Although a computer 1 that functions as the generation device 200 according to the first embodiment is an example in the following explanation, the same holds for each of the corresponding devices in the second and the third embodiments.

As illustrated in FIG. 21, the computer 1 includes a processor 101 that executes various types of arithmetic processing; an input device 102 that receives data input; a monitor 103; and a speaker 104. Furthermore, the computer 1 includes a medium reading device 105 that reads programs, and the like, from a storage medium; an interface device 106 for connecting to various devices; and a communication device 107 for communication connection with an external device via a wired line or wirelessly. Moreover, the computer 1 includes a memory 108 that temporarily stores various types of information; and a hard disk device 109. Further, each unit (101 to 109) in the computer 1 is connected to a bus 110.

Examples of the processor 101 include a microcomputer such as CPU (Central Processing Unit), MPU (Micro Processing Unit), or MCU (Micro Controller Unit). Examples of the processor 101 may be a DSP (Digital Signal Processor), ASIC (Application Specific Integrated Circuit), FPGA (Field Programmable Gate Array), or PLD (Programmable Logic Device). Furthermore, examples of the memory 108 include RAM (Random Access Memory) such as SDRAM (Synchronous Dynamic Random Access Memory), ROM (Read Only Memory), or flash memory.

The hard disk device 109 stores a program 111 for executing various processes in the graph extracting unit 231, the determining unit 232, the virtual-node generating unit 233, and the output unit 234 explained in the above embodiment. Furthermore, the hard disk device 109 stores various types of data 112 (the reference target DB 221, the reference source DB 222, the relationship DB 223, the virtual node DB 224, and the like) that is referred to by the program 111. The input device 102 receives input of operation information from for example the operator of the computer 1. The monitor 103 displays, for example, various screens operated by the operator. The interface device 106 is coupled to, for example, a copier. The communication device 107 is coupled to a communication network, such as LAN (Local Area Network), and communicates various types of information with an external device via the communication network. The input device 102, the monitor 103, the interface device 106, and the communication device 107 correspond to the external I/F 210 that is described in explanation of each functional unit.

The processor 101 reads the program 111 stored in the hard disk device 109, loads it into the memory 108, and executes it, thereby performing various processes. Furthermore, the program 111 does not need to be stored in the hard disk device 109. For example, the computer 1 may read and execute the program 111 stored in a readable storage medium. The storage medium readable by the computer 1 is equivalent to, for example, portable recording medium such as CD-ROM, DVD (Digital Versatile Disk), or USB (Universal Serial Bus) memory, semiconductor memory such as flash memory, or a hard disk drive. Moreover, the program 111 may be stored in a device connected to a public network, the Internet, LAN, or the like, and the program 111 may be read from it and executed by the computer 1.

According to one aspect, the amount of data indicating a correspondence relationship may be reduced.

All examples and conditional language recited herein are intended for pedagogical purposes of aiding the reader in understanding the invention and the concepts contributed by the inventors to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A data generation method comprising:
    extracting, from a database that stores reference source data, reference target data and relationships between the reference target data and the reference source data with regard to a target in which a plurality of sets of the reference source data and the reference target data are connectable by using edges, a first part that forms a complete bipartite graph from the target; and
    when there are multiple sets of the reference source data and multiple sets of the reference target data, included in the first part, that respectively constitute complete bipartite graphs,
    calculating, by a processor for each of the complete bipartite graphs in the first part, a first number of first edges connecting a reference source data set and a reference target data set via a potential virtual node, a second number of second edges directly connecting the reference source data set and the reference target data set, and a third number of reduced edges by subtracting the first number from the second number,
    selecting, by the processor, a second part corresponding to one of the complete bipartite graphs in the first part having the third number that is largest,
    generating for the second part a virtual node between the reference source data set and the reference target data set, by the processor, and
    updating, by the processor, the database by replacing an existing relationship between the reference target data set and the reference source data set in the second part with a new relationship between the reference target data set and the reference source data set via the virtual node,
    taking a relationship among the updated reference source data set, the reference target data set, and the virtual node as input, by a learning device having a neural network,
    comparing an output result corresponding to the input from the neural network with supervised data that corresponds to the relationship, by the learning device, and
    updating weights in sequence from an intermediate layer of the neural network to an input layer, wherein the updating of the weights reduces an error between the two sets of data, by the learning device.

2. The data generation method according to claim 1, further including:
    determining whether there is a plurality of sets of the reference target data with respect to the reference source data included in the complete bipartite graph and whether there is a plurality of sets of the reference source data with respect to the reference target data; and
    retaining an edge connecting the reference source data and the reference target data without generating the virtual node when it is determined that, with respect to at least any one of the reference source data and the reference target data included in the complete bipartite graph, another one thereof is one in number.

3. The data generation method according to claim 1, wherein information relating the reference source data set and the reference target data set is replaced with information relating the reference source data set and the virtual node and information relating the reference target data set and the virtual node.

4. The data generation method according to claim 3, wherein the information relating the reference source data set and the virtual node further includes information indicating a relationship between the reference source data set and the virtual node and the information relating the reference target data set and the virtual node further includes information indicating a relationship between the reference target data and set the virtual node.

5. The data generation method according to claim 1, wherein said extracting extracts the first part that forms the complete bipartite graph connecting the reference target data and the reference source data included in a range in which each set of the reference source data is connected to every set of the reference target data with a single edge and each set of the reference target data is connected to every set of the reference source data with a single edge.

6. The data generation method according to claim 1, wherein said extracting the complete bipartite graph includes specifying a first start position coordinate and a first end position coordinate of a first region that corresponds to the reference source data, and specifying a second start position coordinate and a second end position coordinate of a second region that corresponds to the reference target data.

7. The data generation method according to claim 6, wherein when at least three regions are extracted, said generating of the virtual node excludes a third part of the at least three extracted regions.

8. The data generation method according to claim 1, wherein said extracting the complete bipartite graph is based on the reference target data of a protein or a gene region in a genome sequence and the reference source data related to amino acid substitution or a variant of a base.

9. The data generation method according to claim 1, wherein said generating the virtual node between the reference source data set and the reference target data set is performed when a total number of reference target nodes and reference source nodes is at least six and the multiple sets of the reference source data and the multiple sets of the reference target data in the complete bipartite graph are included in the first part.

10. A non-transitory computer-readable recording medium storing therein a data generation program that causes a computer to execute a process comprising:
  extracting, from a database that stores reference source data, reference target data and relationships between the reference target data and the reference source data with regard to a target in which a plurality of sets of the reference source data and the reference target data are connectable by using edges, a first part that forms a complete bipartite graph from the target; and
  when there are multiple sets of the reference source data and multiple sets of the reference target data, included in the first part, that respectively constitute complete bipartite graphs,
    calculating, by a processor for each of the complete bipartite graphs in the first part, a first number of first edges connecting a reference source data set and a reference target data set via a potential virtual node, a second number of second edges directly connecting the reference source data set and the reference target data set, and a third number of reduced edges by subtracting the first number from the second number,
    selecting, by the processor, a second part corresponding to one of the complete bipartite graphs in the first part having the third number that is largest,
    generating for the second part a virtual node between the reference source data set and the reference target data set, and
    updating the database by replacing an existing relationship between the reference target data set and the reference source data set in the second part with a new relationship between the reference target data set and the reference source data set via the virtual node,
  taking a relationship among the updated reference source data set, the reference target data set, and the virtual node as input, by a learning device having a neural network,
  comparing an output result corresponding to the input from the neural network with supervised data that corresponds to the relationship, by the learning device, and
  updating weights in sequence from an intermediate layer of the neural network to an input layer, wherein the updating of the weights reduces an error between the two sets of data, by the learning device.

11. A data generation apparatus comprising:
  a memory storing reference source data, reference target data and relationships between the reference target data and the reference source data in a database;
  a processor, coupled to the memory, configured to:
    extract, from the database with regard to a target in which a plurality of sets of the reference source data and the reference target data are connectable by using edges, a first part that forms a complete bipartite graph from the target; and
    when there are multiple sets of the reference source data and multiple sets of the reference target data, included in the first part, that respectively constitute complete bipartite graphs,
      calculate, for each of the complete bipartite graphs in the first part, a first number of first edges connecting a reference source data set and a reference target data set via a potential virtual node, a second number of second edges directly connecting the reference source data set and the reference target data set, and a third number of reduced edges by subtracting the first number from the second number,
      select a second part corresponding to one of the complete bipartite graphs in the first part having the third number that is largest,
      generate for the second part a virtual node between the reference source data set and the reference target data set, and
      update the database by replacing an existing relationship between the reference target data set and the reference source data set in the second part with a new relationship between the reference target data set and the reference source data set via the virtual node; and
  a learning device having a neural network, configured to
    take a relationship among the updated reference source data set, the reference target data set, and the virtual node as input,
    compare an output result corresponding to the input from a neural network with supervised data that corresponds to the relationship, and
    update weights in sequence from an intermediate layer of the neural network to an input layer, wherein an error between the two sets of data is reduced by updating the weights.

* * * * *